United States Patent
McCully

(10) Patent No.: US 6,696,082 B2
(45) Date of Patent: Feb. 24, 2004

(54) ENHANCED LIPOSOMAL THIORETINACO OZONIDE COMPOSITIONS AND LIPOSOMAL CARRIER

(76) Inventor: Kilmer S. McCully, 15 Wildwood St., Winchester, MA (US) 01890-1735

(*) Notice: Subject to any disclaimer, the term of this patent is extended or adjusted under 35 U.S.C. 154(b) by 104 days.

(21) Appl. No.: 10/038,913

(22) Filed: Jan. 8, 2002

(65) Prior Publication Data

US 2003/0157158 A1 Aug. 21, 2003

(51) Int. Cl.$^7$ ............................................. A61K 9/127
(52) U.S. Cl. ........................................................ 424/450
(58) Field of Search ..................... 424/450; 536/26.4; 549/3; 556/138; 514/725, 184, 185, 52, 47

(56) References Cited

U.S. PATENT DOCUMENTS

| | | | | |
|---|---|---|---|---|
| 5,527,528 A | * | 6/1996 | Allen | |
| 5,565,558 A | * | 10/1996 | McCully | |
| 5,811,119 A | * | 9/1998 | Mehta | |
| 6,054,595 A | * | 4/2000 | Kazimir | |

* cited by examiner

*Primary Examiner*—Gollamudi S. Kishore
(74) *Attorney, Agent, or Firm*—William D. Breneman, Esq.; Peter J. Gorges, Esq.; Breneman & Georges

(57) ABSTRACT

A therapeutically active composition of thioretinaco ozonide is provided for providing anticarcinogenic, antineoplastic, antiviral, antiatherogenic, and antiaging benefits having the formula:

$$(NHTR)_2 CblO_3 O_2 ATP$$

wherein:
NHTR is N-homocysteine thiolactonyl retinamide;
Cbl is cobalamin;
$O_3$ is ozone;
$O_2$ is oxygen; and
ATP is adenosine triphosphate.

The N-homocysteine thiolactonyl retinamido cobalamin ozonide oxygen adenosine triphosphate complex is further enhanced by utilizing an ozone-resistant liposomal carrier for protecting the composition against oxidative degradation. The ozone-resistant liposomal carrier is advantageously employed to protect a variety of pharmaceutical compositions from oxidative degradation. The ozone-resistant liposomal carrier can also be sterically stabilized to increase the concentration and efficiency of the delivery of pharmaceutical compositions.

6 Claims, No Drawings

ENHANCED LIPOSOMAL THIORETINACO OZONIDE COMPOSITIONS AND LIPOSOMAL CARRIER

BACKGROUND OF THE INVENTION

1. Field of the Invention

The invention pertains to the enhancement of the anticarcinogenic, antineoplastic, antiviral, antiatherogenic, and antiaging activities of thioretinaco ozonide by use of specialized liposomal carrier particles containing oxygen, adenosine triphosphate, and glycolipids, phosphatides and sterols in which all carbon—carbon bonds are fully saturated with hydrogen.

2. Description of the Related Art Including Information Disclosed Under 37 CFR 1.97 and 1.98

Homocysteine thiolactone, a metabolite of the essential amino acid, methionine, is metabolized abnormally in malignant cells, as reported in *Cancer Research* 36:3198–3202, 1976. Unlike normal cells or cells lacking cystathionine synthase, which rapidly complete this conversion, malignant cells are unable to metabolize homocysteine thiolactone to sulfate ions. Because of this abnormality, homocysteine thiolactone accumulates within malignant cells and reacts with the free amino groups of proteins, nucleic acids, glycosaminoglycans, and other macromolecules. As the result of this reaction, peptide bonds are formed between homocysteine thiolactone and the free amino groups of macromolecules, a process known as homocysteinylation. Extracts of human tumors contain free homocysteine thiolactone, as demonstrated by chromatographic separation and detection by column and thin layer chromatography, as reported in *Research Communications in Chemical Pathology and Pharmacology* 59:107–119, 1988. Free homocysteine thiolactone is present in cultured malignant cells, but only trace amounts are found in normal cells and tissues. The formation of homocysteine thiolactone from methionine is catalyzed by methionyl tRNA synthase by an error editing reaction, as reported in *FEBS Letters* 317:237–240, 1993.

In addition to the abnormality of conversion of homocysteine thiolactone to sulfate, malignant cells also possess other characteristic abnormalities of methionine metabolism, as described in *Annals of Clinical and Laboratory Science* 24:27–59, 1994. Malignant cells grow very slowly in media that are free of methionine when supplemented by homocysteine and a source of methyl groups, such as methyltetrahydrofolate, whereas non-malignant cells grow normally under these conditions. The ratio of adenosyl methionine to adenosyl homocysteine concentrations in malignant cells is decreased because of decreased synthesis of adenosyl methionine and increased formation of adenosyl homocysteine, as compared with normal cells. As a result, an increased concentration of homocysteine is present in the plasma of many human patients with malignant tumors of different types. Cells and tissues from malignant tumors also contain increased transmethylase activity, and the DNA of malignant tumors are characteristically hypomethylated, as compared with the DNA of normal tissues. The carcinogenic effect of the antimetabolite, ethionine, is counteracted by dietary methionine in experimental animals because of decreased formation of adenosyl ethionine from ethionine and increased formation of adenosyl methionine from methionine. Totally synthetic experimental diets that are deficient in choline and other sources of methyl groups are carcinogenic in animals, and dietary methionine counteracts this carcinogenic effect. Increased concentrations of methionine in the culture medium of malignant or transformed cells inhibit aerobic glycolysis and the production of lactic acid in the presence of oxygen, a characteristic metabolic abnormality of malignant cells.

The cause of abnormal homocysteine thiolactone metabolism in malignant cells was hypothesized to result from a deficiency of or failure to synthesize an N-substituted derivative of homocysteine thiolactone, as discussed in *Cancer Research* 36:3198–3202, 1976. According to this hypothesis, normal cells contain this chemopreventive derivative that facilitates sulfate formation from homocysteine thiolactone. The concentration of this hypothetical chemopreventive derivative is believed to be diminished during the carcinogenic transformation of normal to malignant cells through the action of carcinogenic chemicals, radiation, viruses or other stimuli. The function of this chemopreventive derivative in normal cells is to prevent accumulation of homocysteine thiolactone by catalyzing its conversion to phosphoadenosine phosphosulfate, sulfate esters of glycosaminoglycans, steroids and other compounds, and sulfate ions. As a result of this chemopreventive derivative in metabolic functions, the characteristic metabolic abnormalities of malignancy, which are attributable to excess accumulation of homocysteine thiolactone, are prevented in normal cells. Thus according to this concept, the increased growth rate, the aggregation of nucleoproteins, the increased expression of developmentally suppressed genes, the degradation of cellular membranes and the abnormalities of oxidative metabolism, such as aerobic glycolysis, are all attributable to increased accumulation of homocysteine thiolactone resulting from depletion of the chemopreventive derivative within malignant cells.

The identity of the N-substituted derivative of homocysteine thiolactone that prevents growth of malignant tumors in animals was elucidated by organic synthesis of antineoplastic compounds containing homocysteine thiolactone. As described in U.S. Pat. No. 4,383,994, N-maleyl homocysteine thiolactone amide, N-maleamide homocysteine thiolactone amide, and rhodium trichloride oxalyl homocysteine thiolactone amide suppress the growth of malignant tumors in animals. Encapsulation of N-maleamide homocysteine thiolactone amide within liposomes greatly enhances its antineoplastic activity, as reported in *Proceedings of the Society for Experimental Biology and Medicine* 180:57–61, 1985. Structural analysis of these biologically active derivatives of homocysteine thiolactone suggests that the hypothetical chemopreventive derivative is (1) active in a lipid-soluble form, (2) contains a conjugated double bond system with a carbonyl group adjacent to the nitrogen atom of homocysteine thiolactone, and (3) forms a complex with a transition metal atom that enhances antineoplastic activity.

U.S. Pat. Nos. 4,618,685 and 4,925,931, describe the reaction of homocysteine thiolactone with retinoic acid to form N-homocysteine thiolactonyl retinamide (NHTR), known as thioretinamide, and thioretinamide reacts with cobalamin to form N-homocysteine thiolactonyl retinamido cobalamin $(NHTR)_2Cbl$, known as thioretinaco. Both thioretinamide and thioretinaco have anticarcinogenic and antineoplastic activities, as reported in *Carcinogenesis* 8: 1559–1562, 1987 and in *Proceedings of the Society for Experimental Biology and Medicine* 191:346–351,1989. The method of synthesis of thioretinamide was significantly improved by use of N-ethyl-N'-(3-dimethyl-aminopropyl) carbodiimide in the reaction mixture, discussed in U.S. Pat. No. 6,054,595. This method replaces the conjugation agent, dicyclohexyl carbodiimide, in the reaction mixture of the original method and produces pure thioretinamide in high yield, approximately 72% of theoretical yield. This highly pure thioretinamide and its complex with cobalamin, thioretinaco, have antiatherogenic activity in rats treated with parenteral homocysteine thiolactone, as reported by M. Kazimir in MS Thesis, Baylor University, 1999.

In experiments with cultured malignant and normal cells thioretinamide and thioretinaco were demonstrated to decrease growth without degeneration or detachment of the cells from the culture dish, except at high concentrations, as reported in *Research Communications in Chemical Pathology and Pharmacology* 77:125–128, 1992. Intra-tumor administration of thioretinaco decreased the growth of human pancreatic adenocarcinomas in athymic mice, as reported in *Research Communications in Chemical Pathology and Pharmacology* 66:117–122, 1989.

In U.S. Pat. No. 5,565,558, the biological activity of thioretinaco is enhanced by ozone in combination with interferon. Ozone is believed to form an ozone bridge between the two sulfur atoms of thioretinaco, producing a disulfonium complex that catalyzes oxidative phosphorylation, as discussed in *Annals of Clinical and Laboratory Science* 24:27–59, 1994. Because of its lipophilic thioretinamide groups, thioretinaco is bound to the lipid bilayer of normal cells, contains tetraene conjugated double bond systems and carbonyl groups adjacent to the nitrogen atoms of the thioretinamide groups, which form an octahedral complex with the cobalt atom of cobalamin. During oxidative phosphorylation, thioretinaco forms a thioretinaco ozonide disulfonium complex with ozone, oxygen and adenosine triphosphate (ATP) within mitochondrial membranes. According to this concept, electrons from electron transport particles and protons from F1FO complexes, in the presence of dehydroascorbate, successively reduce the oxygen molecule that is bound to thioretinaco ozonide, catalyzing the stereospecific binding and release of ATP from the ATP synthetase of F1 complexes. By transporting electrons from free radical compounds to its oxygen atom, the thioretinaco ozonide disulfonium complex prevents oxidative damage to cellular macromolecules in normal cells. In cells with reduced concentrations of thioretinaco ozonide within cellular membranes, such as cells from neoplastic, atherosclerotic, virally infected, or senescent tissues, increased oxidative damage to macromolecules results from failure to transport electrons from free radical compounds to oxygen during oxidative phosphorylation.

Another important function of thioretinaco ozonide in normal cells is believed to be the stereospecific synthesis of 1-adenosyl methionine from methionine and ATP that is bound to the ATP synthetase of F1 complexes of mitochondrial membranes, as reviewed in *Annals of Clinical and Laboratory Science* 24:134–152, 1994. During cell division and growth of normal tissues, thioretinaco is believed to be reversibly converted to thioco, increasing intracellular free radical oxidants, and oxidizing glutathione and ascorbate. Thioco is the complex formed from homocysteine thiolactone and cobalamin. In this process, reactive oxygen compounds, such as superoxide, oxidize the sulfur atom of homocysteine thiolactone to sulfate, the precursor of the coenzyme, phosphoadenosine phosphosulfate. This coenzyme sulfates the glycosaminoglycans of connective tissues during tissue growth.

The efficiency of homocysteine thiolactone metabolism declines with aging, explaining increased synthesis of homocysteine thiolactone, increased serum homocysteine concentration, and decreased serum adenosyl methionine concentration during aging. These observations suggest and indicate that thioretinaco ozonide is gradually lost from cellular membranes during the aging process. According to this precept, the increased risk of atherogenesis and carcinogenesis with aging is related to increased susceptibility to loss of thioretinaco ozonide from cellular membranes because of atherogenic factors or because of carcinogenic factors.

Recombinant interferon gamma increases the intracellular content of adenosyl methionine in cultured macrophages, as reported in *Journal of Immunology* 136:2595–2604, 1986. In that study, the enhanced tumoricidal activity of macrophages activated by interferon gamma was attributed to increased intracellular adenosyl methionine. Methionine and retinoic acid enhance the antiproliferative effects of interferons alpha and beta in transformed and malignant cultured cells, as reported in *Journal of Biological Regulators and Homeostatic Agents* 2:45–49, 1988. Induction of interferon by poly I:C in mice exposed to ozone reduces the extent of lung damage, and anti-interferon antibody increases lung damage by ozone, demonstrating an antioxidant activity of interferon, as reported in *Toxicology Letters* 39:51–62, 1987.

U.S. Pat. No. 5,565,558 discloses that the simultaneous administration of alpha-, beta-, or gamma-interferons enhances the therapeutic activity of thioretinaco ozonide disulfonium complex. Alpha-, beta-, and gamma-interferons are cytokines with well-known antineoplastic, antiviral, and antiproliferative activities. The use of interferons in human subjects, however, has the disadvantage of systemic toxicity from the inflammatory effects of these cytokines. Although there is enhancement of therapeutic activity of these compounds from activation of the immune system by interferons, the side effects may be deleterious in some human subjects.

Ozone selectively inhibits the growth of human cancer cells in culture, compared with its effect on the growth of normal human lung diploid fibroblasts, as reported in *Science* 209:931–933, 1980. Ozone decreases the carcinogenicity of urethane in producing pulmonary tumors in mice in a dose dependent manner, as reported in *Journal of the National Cancer Institute* 78: 149–154, 1987. Treatment of rats with ozone increases the production of nitric oxide by inducible nitric oxide synthetase of pulmonary macrophages, and more nitric oxide is produced in rats treated with interferon gamma, as reported in *Journal of Immunology* 151:7196–7205, 1993. Synthesis of nitric oxide from arginine is believed to be responsible for the tumoricidal effect of activated macrophages, as reported in *Cancer Research* 50:1421–1425, 1990. Nitric oxide is a free radical gas molecule that acts as a mediator of smooth muscle cell relaxation and inhibitor of platelet aggregation. Nitric oxide may interact with thioretinaco ozonide disulfonium complex to inhibit oxidative metabolism and induce cellular degeneration within malignant cells due to the low concentration of thioretinaco ozonide within cellular membranes of these cells.

In order to administer thioretinamide, thioretinaco, or thioretinaco ozonide to animals or human subjects a suitable solvent or pharmaceutical carrier is required. Thioretinaco and thioretinaco ozonide are potentially unstable complexes that may become dissociated within the body, leading to inhibition of therapeutic activity. Furthermore, ozone is a highly reactive oxidant gas that can degrade the molecular constituents of vehicles, causing loss of biological activity. Previously, various pharmaceutical carriers have been employed to deliver these compounds to animals treated with carcinogenic chemicals, animals with transplanted malignant neoplasms, or animals with arteriosclerotic plaques. For use in human subjects these pharmaceutical carriers must be non-toxic, stable, and capable of transporting these compounds without dissociation or degradation to the site of action within cells and tissues of the body. Use of pharmaceutical carriers such as propylene glycol and dimethyl sulfoxide to dissolve thioretinamide, thioretinaco or thioretinaco ozonide may result in partial loss of therapeutic activity because of dissociation of the thioretinaco ozonide disulfonium complex within the cells and tissues of the body.

Both conventional liposomes and sterically-stabilized liposomes have been studied extensively in animal models and in human trials for delivery of a wide variety of biologically and therapeutically active compounds, as reviewed in *Pharmacological Reviews* 51:691–743, 1999. In general liposomal delivery systems are capable of delivering a drug or specialized pharmaceutical compound to a tissue of the body which is supplied by blood vessels of increased permeability. Blood vessels supplying tumors or blood vessels supplying tissues with inflammatory reactions are typically characterized by increased permeability. The use of sterically stabilized liposomes for delivery of biologically active compounds has the advantage of prolongation of the half-life, higher blood levels, and decreased volume of distribution within the body. Furthermore, the use of polyethyleneglycol polymers in the formation of sterically stabilized liposomes decreases uptake by macrophages of the reticulo-endothelial system. This action prolongs the half-life of liposomes and increases the blood levels of liposomes and their pharmaceutical contents.

Liposome formulations containing a negatively charged glycolipid, such as phosphatidylinositol, and a neutral phospholipid, such as distearoyl phosphatidylcholine, yield a prolonged circulation time in blood of mice with transplanted tumors, as reported in *Proceedings of the National Academy of Sciences USA* 85:6949–6953, 1988. Liposome formulations incorporating a synthetic polyethyleneglycol-derivatized phospholipid, such as polyethyleneglycol-conjugated distearoyl phosphatidyl ethanolamine, exhibit increased circulation time, decreased uptake by liver and spleen, and increased uptake by transplanted tumors in mice, as reported in *Proceedings of the National Academy of Sciences USA* 88: 11460–11464, 1991. Extrusion of liposomes through polycarbonate membranes yields liposomal particles of defined size distribution, as reported in *Biochimica et Biophysica Acta* 557:9–23, 1979. The use of liposome formulations that are sterically stabilized increases the circulation time and delivery of pharmaceutical agents to tumor tissue or tissues with highly permeable blood vessels, such as those found in granulation tissue and inflammatory tissues, as discussed in *Bioconjugate Chemistry* 9:418–450, 1998.

In the prior art Yamauchi et al, published application US2001/000,648 discloses the use of sphingolipids containing sphingosine as a major constituent of liposomal carriers. The object of this approach is to improve stability of drugs which have poor stability in their aqueous solution. The use of sphingolipids as constituents of liposomal carriers for drugs with oxidizing properties, such as thioretinaco ozonide, would not be useful. The reason is that the unsaturated carbon—carbon double bond of sphingosine would make the liposomal formulation susceptible to ozonolysis or oxidative degradation by thioretinaco ozonide or other pharmaceutical preparations with oxidizing properties.

SUMMARY OF THE INVENTION

The invention provides a therapeutically active composition of thioretinaco ozonide complexed in an ozone-resistant liposome, providing anticarcinogenic, antineoplastic, antiviral, antiatherogenic, and antiaging benefits. The novel therapeutically active composition has the formula:

$$(NHTR)_2 CblO_3 O_2 ATP$$

wherein:
NHTR is N-homocysteine thiolactonyl retinamide;
Cbl is cobalamin;
$O_3$ is ozone;
$O_2$ is oxygen; and
ATP is adenosine triphosphate.

The advantages of the novel N-homocysteine thiolactonyl retinamido cobalamin ozonide oxygen adenosine triphosphate complex are further enhanced by utilizing an ozone-resistant liposomal carrier in which all lipids, including glycolipids, phosphatides, and sterols, have all carbon—carbon bonds fully saturated with hydrogen. The ozone-resistant liposomal (OR-L) carrier can also be sterically stabilized to produce ozone-resistant sterically stabilized liposomal (OR-SSL) carriers.

The novel ozone-resistant liposomal carriers can be advantageously employed to protect a wide variety of medicaments or pharmaceutical compositions from oxidative degradation. The protection of medicaments and pharmaceutical compositions is further enhanced by the use of sterically stabilized ozone-resistant liposomes, which increase the concentration and efficiency of the delivery of the pharmaceutical composition, drug or medicament to the diseased cell or tissue. More particularly, the advantages of the invention are in the best mode achieved by the use of medicaments or pharmaceutical compositions with the ozone-resistant liposome carrier where the medicament is selected from the oxidative degradation susceptible drugs selected from the group comprising:

(1) N-homocysteine thiolactonyl retinamide (NHTR)
(2) N-homocysteine thiolactonyl retinamido cobalamin $(NHTR)_2 Cbl$;
(3) N-homocysteine thioretinaco ozonide (NHTR)$_2 CblO_3$; and
(4) N-homocysteine thioretinaco ozonide oxygen adenosine triphosphate disulfonium complex (NHTR)$_2 CblO_3 O_2 ATP$.

The novel medicaments or pharmaceutical preparations, including the ozone-resistant liposomal carrier, can be administered to an animal in need thereof, to treat a wide variety of carcinogenic, neoplastic, viral, atherogenic, and aging conditions. The novel medicaments or pharmaceutical preparations, including the ozone-resistant liposomal carrier can be administered enterically, parenterally, intravenously, intramuscularly, intraperitoneally, subcutaneously, intracisternally, intrathecally, and within neoplasms by direct injection. The compositions of the invention may also be mixed with well-known incipients and inert carriers to form time release formulations, to form suspensions, emulsions, and dispersions used for the administration of pharmaceutical preparations, drugs, or medicaments in accordance with the invention.

DETAILED DESCRIPTION OF THE INVENTION

One embodiment of the invention pertains to a therapeutically active form of thioretinaco ozonide that is complexed with oxygen and adenosine triphosphate within liposomes for delivery to diseased cells and tissues of the body. The use of liposomes enhances the therapeutic activity of the thioretinaco ozonide disulfonium complex because of its stabilization in a lipid-soluble form. The novel use of adenosine triphosphate prevents dissociation of the complex because of stabilization by stereospecific binding to the ozone oxygen ion cluster of the thioretinaco ozonide disulfonium complex. Furthermore, this invention prevents further dissociation of thioretinaco into thioretinamide and cobalamin by stabilization of the thioretinaco ozonide oxygen adenosine triphosphate complex within the liposomal delivery system. Prevention of dissociation of the thioretinaco ozonide disulfonium complex by this invention enhances its therapeutic action within diseased cells and tissues.

A further embodiment of the invention overcomes the loss of therapeutic activity resulting from oxidative degradation of liposomal glycolipids, phosphatides, and sterols by ozone. Oxidative degradation of liposomal glycolipids, phosphatides and sterols is prevented by use of liposomes in which these constituents contain carbon—carbon bonds that are fully saturated with hydrogen. For example, the use of hydrogenated phosphoinositol, distearoyl phosphatide, and cholestanol in liposomes protects liposomal integrity against degradation by ozone. Thus this specialized liposomal delivery system prevents oxidative damage to liposomal constituents by ozone because lipids with saturated carbon—carbon double bonds are resistant to ozonolysis.

The use of polyethyleneglycol derivatized to hydrogenated phosphatidylcholine or to hydrogenated phosphatidylethanolamine produces sterically stabilized liposomes that are suitable for carrying thioretinaco ozonide, oxygen and adenosine triphosphate in the form of thioretinaco ozonide disulfonium complex. These liposome preparations have the advantage of a prolonged half-life, increased blood levels, and decreased volume of distribution within the body. Moreover, these sterically stabilized liposomes have a reduced uptake by phagocytic cells of liver and spleen and increased uptake by cells and tissues of malignant tumors or inflammatory tissues, because of increased permeability of blood vessels in these tissues. The use of glycolipids, phosphatides and sterols in which all carbon—carbon double bonds are saturated with hydrogen in sterically stabilized liposomes protects against oxidative degradation by ozone.

In accordance with a further embodiment of the invention, thioretinaco ozonide that is complexed with oxygen and adenosine triphosphate within sterically stabilized, ozone-resistant liposomes increases the concentration of thioretinaco ozonide disulfonium complex within diseased cells and tissues. This novel method of stabilization and delivery of the thioretinaco ozonide disulfonium complex has the effect of greatly enhancing the biological and therapeutic effects of this complex. Thioretinamide, thioretinaco, and thioretinaco ozonide are non-toxic within normal cells and tissues. Through the use of the invention, thioretinaco ozonide can be delivered to the site of action within the membranes of diseased cells and tissues without toxicity to surrounding normal cells and tissues. Furthermore, the use of cytokines, such as alpha-, beta-, or gamma-interferon can be minimized or eliminated for enhanced therapeutic effects, increasing the usefulness of liposomal thioretinaco ozonide for therapy of a wide range of degenerative diseases of aging.

As a result of the delivery of an increased concentration of thioretinaco ozonide oxygen disulfonium complex to diseased cells and tissues through the use of the invention, greatly enhanced therapeutic effects are observed. These effects are useful in therapy of diseases such as cancer, arteriosclerosis, viral infections, inflammatory diseases, autoimmune disease, and degenerative diseases of aging. As a result of the invention, the accumulation of reactive oxygen radicals within diseased cells are diminished. Due to the decreased formation of homocysteine thiolactone from methionine, the homocysteinylation of proteins, nucleic acids, and glycosaminoglycans by homocysteine thiolactone is diminished. Thioco is converted to thioretinaco, diminishing the growth rate of affected cells. Finally, oxidative phosphorylation is increased, reversing the biochemical abnormalities of neoplastic cells, myointimal cells of atheromas, virally infected cells, and senescent cells. The invention corrects the metabolic abnormalities of diseased cells by use of liposomal thioretinaco ozonide to increase the concentration of thioretinaco ozonide disulfonium complex within cells and tissues, restoring them to a normal state.

Thioretinamide, known as N-homocysteine thiolactonyl retinamide (NHTR), can be prepared, as described in U.S. Pat. Nos. 4,618,685 and 6,054,595, by the reaction of homocysteine thiolactone with retinoic acid. Thioretinaco known as N-homocysteine thiolactonyl retinamido cobalamin $(NHTR)_2Cbl$) can be prepared, as described in U.S. Pat. No. 4,925,931, by reaction of thioretinamide with 5' deoxyadenosyl cobalamin (Cbl). Thioretinaco ozonide $(NHTR_2CblO_3)$ can be prepared, as described in U.S. Pat. No. 5,565,558 by reaction of ozone with thioretinaco.

Specialized liposomal carrier particles, ozone-resistant liposomes (OR-L) are formed from hydrogenated phosphoinositol (HPI), distearoyl phosphatidylcholine (DSPC), cholestanol (CHA) and coenzyme Q10 (Q10), as follows:

$$HPI+DSPC+CHA+Q10 \rightarrow OR-L$$

Sterically stabilized liposomal carrier particles, ozone-resistant, sterically stabilized liposomes (OR-SSL) are formed from polyethyleneglycol derivatized distearoyl phosphatidyl ethanolamine (PEG-DSPE), hydrogenated phosphatidyl choline (HPC), cholestanol (CHA) and coenzyme Q10 (Q10), as follows:

$$HPC+PEG-DSPE+CHA+Q10 \rightarrow OR-SSL$$

Other suitable hydrogenated glycolipids (HGL), saturated phosphatides (SP), polyethyleneglycol-derivatized phosphatides (PEG-P), and hydrogenated sterols (HS) can be employed in a similar manner to produce comparable ozone-resistant, sterically stabilized liposomal carrier particles, as follows:

$$HGL+SP+PEG-P+HS+Q1O \rightarrow OR-SSL$$

In one embodiment of the invention, ozone-resistant liposomes (OR-L) are loaded with thioretinaco ozonide disulfonium complex $(NHTR)_2CblO_3^{++}$, oxygen, and adenosine triphosphate (ATP) in equimolar amounts, as follows:

$$(NHTR)_2CblO_3^{++}+O_2+ATP^{2-}+OR-L \rightarrow (NHTR)_2CblO_3O_2ATP(OR-L)$$

The ozone-resistant liposomes contain the thioretinaco ozonide oxygen disulfonium complex stereospecifically bound to ATP.

In a further embodiment of the invention, sterically stabilized, ozone-resistant liposomes (OR-SSL) are loaded with thioretinaco ozonide oxygen disulfonium complex $(NHTR)_2CblO_3^{++}$, oxygen, and adenosine triphosphate (ATP) in equimolar amounts, as follows:

$$(NHTR)_2CblO_3^{++}+O_2+ATP^{2-}+OR-SSL \rightarrow (NHTR)_2CblO_3O_2ATP(OR-SSL)$$

The ozone-resistant, sterically stabilized liposomes contain the thioretinaco oxygen disulfonium complex stereospecifically bound to ATP.

The therapeutic effect of the invention is accomplished by administering the ozone-resistant liposomes containing the thioretinaco oxygen disulfonium complex stereospecifically bound to ATP to diseased cells and tissues of mammals. The administration can be accomplished by intravenous, oral, subcutaneous, intraperitoneal, intramuscular or transdermal routes. The administration can also be accomplished by direct injection into diseased tissues, using computerized tomographic scanning, ultrasound scanning, magnetic resonance scanning, or similar methods.

The advantage of the specialized liposomal delivery system of the invention is that the thioretinaco ozonide oxygen disulfonium complex which is stereospecifically bound to ATP becomes incorporated within the cellular membranes of diseased cells and tissues. The lipid phase of the liposomal particles facilitates the binding to cellular membranes because of their high content of lipids of similar composition.

In mammals exposed to carcinogenic chemicals, radiation, or oncogenic viruses, the subject specialized liposomal particles of this invention, containing stabilized thioretinaco ozonide oxygen disulfonium adenosine triphosphate complex, $(NHTR)_2CblO_3O_2ATP$, ameliorate/prevent the induction of benign or malignant neoplasms. In mammals with transplanted or spontaneous primary or metastatic malignant neoplasms, the specialized liposomal particles of this invention inhibit growth and cause regression of these neoplasms. In mammals consuming an atherogenic diet, the specialized liposomal particles of this invention prevent, delay, or cause regression of arteriosclerotic plaques of aorta and peripheral arteries. In mammals that are infected with pathogenic viruses, the specialized liposomal particles of this invention inhibit replication of these viruses, prevent or cause regression of the pathogenic effects of these viruses, and prevent post-infection sequelae of these viruses. In senescent animals with degenerative aging changes of their tissues, decreased oxidative metabolism, and decreased life expectancy, the specialized liposomal particles of this invention prevent further degenerative changes of tissues associated with aging, enhance oxidative metabolism, and prolong life span.

The novel specialized liposomal particles of this invention, containing stabilized thioretinaco ozonide oxygen disulfonium adenosine triphosphate complex, are effective in preventing chemical carcinogenesis in mammals, inhibiting growth of malignant tumors in mammals, decreasing atherogenesis in mammals, decreasing viral replication in cells and tissues of mammals, and extending the life span of mammals. In addition to the efficacy in the aforesaid therapeutic effects, the method of use of the compositions of the present invention is non-toxic. In this respect, the compounds and processes of this invention do not suffer the drawback of many known antineoplastic, antiviral, antiatherogenic, and antiaging agents, which have cumulative toxic effects after prolonged administration.

In accordance with the invention, thioretinaco ozonide, delivered by specialized liposomal particles, prevents the depletion of membrane bound thioretinaco ozonide by carcinogenic chemicals, radiation or viruses. The invention restores the deficient synthesis of adenosyl methionine within malignant cells, virally infected cells, damaged myointimal cells of arteries, or senescent cells by restoring the deficient concentration and deficient formation of thioretinaco ozonide within cellular membranes. The invention also prevents accumulation of homocysteine thiolactone within cells and tissues of mammals, reducing the formation of adenosyl homocysteine, and reducing the release of homocysteine into the blood stream. This invention is effective in lowering blood homocysteine levels in mammals with kidney failure, aging, genetic predisposition, toxic and hormonal abnormalities.

Currently available therapies for acute coronary syndrome are not totally effective in preventing recurrent vascular events. Current therapies with anti-platelet agents, beta-blockers, anticoagulants, thromboplastin activation, calcium channel blockers and angiotensin converting enzyme inhibitors are only partially effective in therapy. Treatment of hyperhomocysteinemia with triple vitamin therapy with B6, folate and B12 is only partially effective over periods of 6–18 months in preliminary trials to prevent plaque progression and recurrent vascular events. Treatment of human subjects with the liposomal thioretinaco ozonide of the invention should arrest and counteract acute coronary syndrome within minutes or hours by restoring the depletion of thioretinaco ozonide disulfonium complex from the membranes of vascular cells, restoring endothelial function, preventing a prothrombotic state, and restoring nitric oxide function. Hyperhomocysteinemia that is characteristic of acute coronary syndrome and chronic arteriosclerosis will be prevented by liposomal thioretinaco ozonide, preventing vascular injury, progression of arteriosclerotic plaques, and recurrent vascular events, such as coronary thrombosis, myocardial infarction, cerebral thrombosis, cerebral infarction, and ischemic gangrene of the extremities.

The delivery of the novel thioretinaco ozonide disulfonium complex within specialized liposomal particles containing oxygen, adenosine triphosphate, and glycolipids, phosphatides, and sterols with saturated carbon—carbon double bonds greatly enhances the therapeutic, anticarcinogenic, antineoplastic, antiatherogenic, and antiproliferative activities against chemical carcinogenesis, neoplastic growth, induction of atherosclerosis, and growth of cultured cancer cells. In contrast, thioretinaco ozonide that is delivered by conventional solvents, such as propylene glycol or dimethyl sulfoxide, has a reduced therapeutic activity because of dissociation of the constituents of the thioretinaco ozonide disulfonium complex within diseased cells and tissues of the body.

The novel compositions of the invention find utility in treatment of mammalian diseases and specifically, are deemed useful in preventing the occurrence of spontaneous human neoplasms, including, but not limited to, cancer of lung, skin, colon, breast, prostate, pancreas, brain, lymph nodes, liver, kidney or other organs that arise because of exposure to carcinogenic chemicals, radiation, viruses, dietary factors, or genetic factors. It is further deemed that the invention is useful for the treatment of human neoplasms, primary or metastatic, by intratumor, oral and parenteral administration, causing regression of and preventing metastasis of malignant neoplasms. It is also deemed that this invention is useful in treatment of human atherosclerosis, involving aorta, coronary, renal, peripheral, cerebral or other major arteries, causing regression of and preventing progression of arteriosclerotic plaques, thereby preventing or ameliorating coronary heart disease, stroke, renovascular disease, and peripheral vascular disease. The invention is deemed useful in treatment of human pathogenic viral infections, including, but not limited to, hepatitis virus, immuno-deficiency virus, hemorrhagic fever viruses, encephalitis viruses, influenza viruses, rhinoviruses, pox viruses, herpetic viruses, and enteric viruses, by preventing viral replication and spread of the virus infection within the cells of the various tissues of the body. The invention is also deemed useful in treatment of human degenerative diseases associated with aging, including, but not limited to, osteoarthritis, osteoporosis, cataract, prostatic hypertrophy, diabetes mellitus, rheumatoid arthritis, thyroiditis, lupus erythematosus, pernicious anemia and other autoimmune disorders, causing remission or preventing progression of these diseases within the tissues of the body. It is expected that this invention will be useful in prolonging human life span by preventing degenerative diseases of aging, including atherosclerosis, cancer, autoimmune disorders, and age-associated loss of function of brain, heart, lungs, liver, kidneys, eyes, ears, and other major organs.

Therapeutic use of the invention allows for decreasing the induction of chemically induced tumors in mammals, decreasing the growth of malignant tumors in mammals, decreasing the induction of arteriosclerotic plaques in mammals, decreasing viral replication in mammals, preventing the degenerative tissue changes associated with aging in mammals, and extending the life span of mammals. Specifically, practice of this invention is considered useful for prevention of spontaneous human neoplasms, including, but not limited to, cancer of lung, skin, breast, prostate, colon, pancreas, brain, lymph nodes, liver, kidney or other organs that arise because of exposure to carcinogenic chemicals, radiation, viruses, dietary factors, or genetic factors.

Applications of the invention are also considered useful for treatment of mammalian and in particular human neoplasms, primary or metastatic, by intratumor, parenteral or enteric administration, for treatment of human atherosclerosis, involving aorta, coronary, carotid, renal, peripheral, or other major arteries, for treatment of human pathogenic viral infections, for treatment of human degenerative diseases associated with aging, including, but not limited to, osteoarthritis, osteoporosis, cataract, prostatic hypertrophy, diabetes mellitus, rheumatoid arthritis, thyroiditis, lupus erythematosus, and pernicious anemia, and for prolonging human life span.

The novel compounds and specialized liposomal delivery systems of the invention can be used in admixture with conventional excipients, i.e., pharmaceutically and physiologically acceptable organic or inorganic carriers suitable for enteral, parenteral, or topical applications that do not deleteriously interact with the active compounds or cause disintegration or degeneration of the liposomal carrier. Suitable pharmaceutically and physiologically acceptable carriers include, but are not limited to, water, salt solutions, alcohols, glycols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidine, etc. The pharmaceutical preparations can be sterilized, and, if desired, mixed with auxiliary agents, including lubricants, preservatives, stabilizers, wetting agents, emulsifiers, salts for influencing osmotic pressure, buffers, coloring, flavoring and/or aromatic substances and the like that do not deleteriously interact with the active compounds. Solutions, suspensions, emulsions, or implants, including suppositories, can conveniently be provided in ampoules for appropriate administration.

As heretofore described, the invention is useful in treatment and prevention of neoplastic, atherosclerotic and viral diseases in mammals, generally, as well as for such treatment in human subjects. The range of useful concentration of liposomal thioretinaco ozonide is broad, extending from 0.1–60 mg/kg of body weight. The subject invention can be administered to mammals or human subjects in the aforesaid dosage range. Suspensions, emulsions and dispersions of the liposomal thioretinaco ozonide particles can be administered by the enteric route, employing capsules and time-release formulations, mixed with suitable inert carriers. The subject invention can also be administered parenterally in compatible solvents and vehicles, given intravenously, intramuscularly, intraperitoneally, subcutaneously, intracisternally, intrathecally, and within neoplasms in various internal organs by direct injection, with ultrasound, nuclear magnetic resonance, or X-ray computerized tomography guidance.

It will be understood by those skilled in the art that the actual preferred amount of the active compound used will vary according to the specific isomer being used, the particular compositions formulated, the mode of application and particular site and organism being treated. Optimal application rates for a given set of conditions can be ascertained by those skilled in the art, using conventional dosage determination tests in accordance with the detailed description of this invention.

The advantages of the invention, as well as aspects of the preferred embodiments, are illustrated more fully in the following Examples:

EXAMPLE 1

To demonstrate anticarcinogenic activity, specialized liposomal thioretinaco ozonide particles that are resistant to ozone are prepared for administration to animals.

Thioretinamide (NHTR) is synthesized from homocysteine thiolactone and retinoic acid, as described in U.S. Pat. No. 4,618,685 and as modified in U.S. Pat. No. 6,054,595.

Thioretinaco $(NHTR)_2Cbl$ is formed by dissolving 0.44 mmol (175.6 mg) of thioretinamide in 1 liter of ethanol at 37° C. and adding 0.22 mmol (347.5 mg) of cobamamide (deoxyadenosyl cobalamin) with mixing under argon atmosphere protected from light, as described in U.S. Pat. No. 4,925,931. The molecular weight of thioretinaco is 2378 (calculated). The molecular weight of cobamamide is 1579.6. The molecular weight of thioretinamide is 399.2. Up to 10 mcl of 12N HCl is added slowly to achieve complete dissolution, yielding a red brown solution. The solution is stirred for 6–12 hours at 37° C. Evaporation of the solvent under reduced pressure yields a bright red orange powder. The UV-visible absorbance spectrum of thioretinaco is different from either thioretinamide or cobamamide between 440 and 800 nm.

Thioretinaco ozonide oxygen adenosine triphosphate disulfonium complex $(NHTR)_2ClO_3O_2ATP$ within ozone-resistant liposomes (OR-L) is prepared by dissolving 0.22 mmol of thioretinaco (525 mg) in 100 ml of Hanks balanced salt solution pH 7.0 containing 0.22 mmol of ATP (disodium adenosine triphosphate, 121 mg). The solution is protected from light and exposed to a closed atmosphere of argon containing 0.22 mmol of ozone (10.56 mg) and 0.22 mmol of oxygen (7.04 mg). The mixture is stirred at 37° C. for 2 hours until complete dissolution yields a clear red-orange-brown solution. The following lipids are dissolved in chloroform in a round bottom flask and deposited on the sides of the flask by evaporation of the solvent. For ozone-resistant liposomes (OR-L), hydrogenated phosphatidyl inositol, 0.22 mmol (155 mg), distearoyl phosphatidylcholine, 2.2 mmol (1554 mg), and cholestanol, 1.1 mmol (425 mg), are utilized (1:10:5 mol/mol). For ozone-resistant sterically stabilized liposomes (OR-SSL), polyethylene glycol-conjugated to distearoyl phosphatidylethanolamine, 0.15 mmol (112 mg), hydrogenated phosphatidylcholine, 1.85 mmol (1462 mg), and cholestanol, 1.0 mmol (386 mg), are utilized (0.15:1.85:1.00 mol/mol). Coenzyme Q10 is added to the lipids in a final concentration of 1% by weight. The thioretinaco ozonide solution is added to the dried lipid film, and liposomes are formed by repeated vortexing. The lipid concentration is adjusted to 15 mg/ml by addition of Hanks solution. The final concentration of thioretinaco ozonide within the liposomes is 2.0 mg/ml. The liposomes are extruded through a polycarbonate membrane, pore size 0.2 micron. The ozone-resistant liposome preparation $(NHTR)_2CblO_3O_2ATP(OR-L)$ and the ozone-resistant sterically stabilized liposome preparation $(NHTR)_2CblO_3O_2ATP(OR-SSL)$ are determined to be sterile, pyrogen-free, and stable at 24° C. The liposomes are 100+/−40 nm in diameter. Cholesterol epoxides and oxides are trace or less by HPLC and thin layer chromatography. The liposomal thioretinaco ozonide preparations are dispensed in sealed ampoules of 10–100 ml.

To demonstrate anticarcinogenic activity A/J female mice are injected with 2 mg of ethyl carbamate in 0.2 ml of water intraperitoneally weekly for 10 weeks, giving a total dose of 20 mg/mammal. The mammals are injected on the following day each week with $(NHTR)_2Cbl$ or $(NHTR)_2CblO_3O_2ATP$ within ozone-resistant liposomes (OR-L) or within ozone-resistant sterically stabilized liposomes (OR-SSL), followed by weekly injections for an additional 16 weeks to make a total of 16 weekly injections. The mammals are weighed weekly, and after 16 weeks the lungs are dissected, fixed in 10% fornalin, and the number of pulmonary tumors is determined by examination with a dissecting microscope. This example illustrates projected percentages of tumors induced, as reflected by anticipated relative values are shown in Table I.

TABLE I

| Compound | Liposome carrier | Total dose (mg/kg) | Tumors induced |
|---|---|---|---|
| (none) | OR-L | — | 100% |
| (none) | OR-SSL | — | 100% |
| $(NHTR)_2Cbl$ | OR-L | 60 | 10% |
| $(NHTR)_2Cbl$ | OR-SSL | 60 | 5% |
| $(NHTR)_2CblO_3O_2ATP$ | OR-L | 60 | <1% |
| $(NHTR)_2CblO_3O_2ATP$ | OR-SSL | 60 | <1% |

Table I demonstrates that the formation of pulmonary neoplasms, induced by ethyl carbamate in A/J mice, is inhibited by use of thioretinaco $(NHTR)_2Cbl$ within ozone-resistant liposomes (OR-L) or within ozone-resistant sterically stabilized liposomes (OR-SSL). Greater inhibition is observed by use of thioretinaco ozonide oxygen ATP disulfonium complex $(NHTR)_2CblO_3O_2ATP$ within ozone-resistant liposomes (OR-L) or within ozone-resistant sterically stabilized liposomes (OR-SSL).

EXAMPLE 2

To demonstrate antineoplastic activity, thioretinaco ozonide oxygen ATP disulfonium complex $(NHTR)_2CblO_3O_2ATP$ within ozone-resistant liposomes (OR-L) and within ozone-resistant sterically stabilized liposomes (OR-SSL) are prepared, as described in Example 1. Human pancreatic adenocarcinoma cells ($10^5$) are injected subcutaneously in athymic mice, producing palpable neoplasms after 10–14 days. The liposome preparations containing thioretinaco or thioretinaco ozonide oxygen ATP disulfonium complex are injected directly into the growing neoplasms. Alternatively, the liposome preparations containing thioretinaco or thioretinaco ozonide oxygen ATP disulfonium complex are injected intraperitoneally each week for 6 weeks, beginning the day after subcutaneous injection of adenocarcinoma cells. After 6 weeks, the mammals are sacrificed, and the tumors are dissected and weighed. As indicated in Table II, tumor weights are reflected by the anticipated relative values shown.

TABLE II

| Compound | Liposome carrier | Total dose (mg/kg) | Tumor weight (g) |
|---|---|---|---|
| (none) | OR-L | — | 1.00 |
| (none) | OR-SSL | — | 1.00 |
| $(NHTR)_2Cbl$ | OR-L | 2.5 intratumor | 0.15 |
| $(NHTR)_2Cbl$ | OR-SSL | 2.5 intratumor | 0.10 |
| $(NHTR)_2CblO_3O_2ATP$ | OR-L | 2.5 intratumor | 0.02 |
| $(NHTR)_2CblO_3O_2ATP$ | OR-SSL | 2.5 intratumor | 0.01 |
| $(NHTR)_2Cbl$ | OR-L | 15 (i.p.) | 0.10 |
| $(NHTR)_2Cbl$ | OR-SSL | 15 (i.p.) | 0.04 |
| $(NHTR)_2CblO_3O_2ATP$ | OR-L | 15 (i.p.) | 0.01 |
| $(NHTR)_2CblO_3O_2ATP$ | OR-SSL | 15 (i.p.) | 0.01 |

The growth of human malignant neoplasms in athymic mice is inhibited by intratumor injection or intraperitoneal injection of thioretinaco within ozone-resistant liposomes or within ozone-resistant sterically stabilized liposomes. Enhanced inhibition of tumor growth is observed by injection of thioretinaco ozonide oxygen ATP disulfonium complex within ozone-resistant liposomes or within ozone-resistant sterically stabilized liposomes.

EXAMPLE 3

To demonstrate antiviral activity, thioretinaco and thioretinaco ozonide oxygen ATP disulfonium complex within ozone-resistant liposomes or within ozone-resistant sterically stabilized liposomes are prepared, as described in Example 1. Cultured mouse L cells are infected with EMC virus at a multiplicity of 10:1. After 14 hours, the culture fluids, containing thioretinaco or thioretinaco ozonide oxygen ATP disulfonium complex, are harvested and assayed for virus particles. As indicated in Table III, virus titers are reflected by the anticipated relative values.

TABLE III

| Compound | Liposome carrier | Concentration (mg/dl) | Virus titer ($\log_{10}$) |
|---|---|---|---|
| (none) | OR-L | — | 2.0 |
| (none) | OR-SSL | — | 2.0 |
| $(NHTR)_2Cbl$ | OR-L | 1.0 | 0.5 |
| $(NHTR)_2Cbl$ | OR-SSL | 1.0 | 0.2 |
| $(NHTR)_2CblO_3O_2ATP$ | OR-L | 1.0 | 0.1 |
| $(NHTR)_2CblO_3O_2ATP$ | OR-SSL | 1.0 | 0.04 |

Viral replication within cultured cells is inhibited by thioretinaco within ozone-resistant or within ozone-resistant sterically stabilized liposomes. Thioretinaco ozonide oxygen ATP disulfonium complex within ozone-resistant liposomes or within ozone-resistant sterically stabilized liposomes is demonstrated to have enhanced antiviral activity.

EXAMPLE 4

To demonstrate antiatherogenic activity, thioretinaco and thioretinaco ozonide oxygen ATP disulfonium complex within ozone-resistant liposomes or within ozone-resistant sterically stabilized liposomes are prepared, as described in Example 1. Rabbits are fed a synthetic diet containing homocystine oxidized with hydrogen peroxide, as described in *Atherosclerosis* 22:215–227, 1975. Weekly injections of thioretinaco or thioretinaco ozonide oxygen ATP disulfonium complex are given within ozone-resistant liposomes or within ozone-resistant sterically stabilized liposomes for 24 weeks. After 24 weeks the mammals are sacrificed, and the percentage of aortic intimal surface involved with arteriosclerotic plaques is determined morphometrically, as described in *Atherosclerosis* 83:197–206, 1990. Relative values for anticipated plaque area percentages are shown in Table IV.

TABLE IV

| Compound | Liposome carrier | Total dose (mg) | Plaque area (%) |
| --- | --- | --- | --- |
| (none) | OR-L | — | 25 |
| (none) | OR-SSL | — | 25 |
| $(NHTR)_2Cbl$ | OR-L | 24 | 5 |
| $(NHTR)_2Cbl$ | OR-SSL | 24 | 3 |
| $(NHTR)_2CblO_3O_2ATP$ | OR-L | 24 | <1 |
| $(NHTR)_2CblO_3O_2ATP$ | OR-SSL | 24 | <1 |

The induction of arteriosclerotic plaques in mammals is inhibited by thioretinaco within ozone-resistant liposomes or within ozone-resistant sterically stabilized liposomes. Thioretinaco ozonide oxygen ATP disulfonium complex within ozone-resistant liposomes or within ozone-resistant sterically stabilized liposomes is demonstrated to have enhanced antiatherogenic activity.

EXAMPLE 5

To demonstrate antiaging activity, thioretinamide and thioretinaco ozonide oxygen ATP disulfonium complex within ozone-resistant liposomes or within ozone-resistant sterically stabilized liposomes are prepared, as in Example 1. Male Wistar rats, aged 400 days, are fed ad libitum (ad lib) or food restricted (FR) diets for 800 days, as described in *Mechanisms of Ageing and Development* 12:161–172, 1980. The mammals are injected intraperitoneally every 20 days with thioretinaco or thioretinaco ozonide oxygen ATP disulfonium complex within ozone-resistant liposomes or within ozone-resistant sterically stabilized liposomes. The approximate anticipated percentages of live mammals, determined at 800 days of age and 1200 days of age, are shown in Table V.

TABLE V

| Diet | Compound | Liposome carrier | total dose (mg/kg) | 800 days (%) | 1200 days (%) |
| --- | --- | --- | --- | --- | --- |
| ad lib | (none) | OR-L | — | 40 | 0 |
| FR | (none) | OR-SSL | — | 60 | 10 |
| ad lib | $(NHTR)_2Cbl$ | OR-L | 40 | 80 | 20 |
| ad lib | $(NHTR)_2Cbl$ | OR-SSL | 40 | 85 | 25 |
| ad lib | $(NHTR)_2CblO_3O_2ATP$ | OR-L | 40 | 95 | 35 |
| ad lib | $(NHTR)_2CblO_3O_2ATP$ | OR-SSL | 40 | 98 | 50 |

The life span of rats is prolonged by intraperitoneal injections of thioretinaco within ozone-resistant liposomes or within ozone-resistant sterically stabilized liposomes. The life span of rats is lengthened to a greater degree by intraperitoneal injections of thioretinaco ozonide oxygen ATP disulfonium complex within ozone-resistant liposomes or within ozone-resistant sterically stabilized liposomes.

EXAMPLE 6

Both thioretinaco and thioretinaco ozonide oxygen ATP disulfonium complex inhibit cell proliferation when added to the culture media within ozone-resistant liposomes or within ozone-resistant sterically stabilized liposomes. These compounds are prepared, as described in Example 1, for addition to cell culture media. Human pancreatic adenocarcinoma cells (RWP-2) are cultured in RPMI 140 medium (Gibco) with 12.5% fetal bovine serum and with added penicillin, streptomycin, fungizone, amphotericin, and garamycin, as described in *Research Communications in Chemical Pathology and Pharmacology* 77:125–128, 1992. The number of cells per dish is determined after culture for 4 days in the presence of thioretinaco or thioretinaco ozonide oxygen ATP disulfonium complex within ozone-resistant liposomes or within ozone-resistant sterically stabilized liposomes, as indicated in Table VI.

TABLE VI

| Compound | Liposome carrier | Concentration (mg/ml) | Cell number ($\times 10^5$) |
| --- | --- | --- | --- |
| (none) | OR-L | — | 7.5 |
| (none) | OR-SSL | — | 7.5 |
| $(NHTR)_2Cbl$ | OR-L | 1.0 | 1.5 |
| $(NHTR)_2Cbl$ | OR-SSL | 1.0 | 1.2 |
| $(NHTR)_2CblO_3O_2ATP$ | OR-L | 1.0 | 0.2 |
| $(NHTR)_2CblO_3O_2ATP$ | OR-SSL | 1.0 | 0.1 |

The growth of human pancreatic adenocarcinoma cells in culture is inhibited, when thioretinaco within ozone-resistant liposomes or within ozone-resistant sterically stabilized liposomes is added to the culture medium. The inhibition of cellular growth is enhanced when thioretinaco ozonide oxygen ATP disulfonium complex within ozone-resistant or within ozone-resistant sterically stabilized liposomes is added to the culture medium. The projected cell number values are illustrative of the expected degree of inhibition that the invention will provide.

Insofar as is known, the D isomer of homocysteine thiolactone possesses biological activity, but to a lesser degree than the L isomer. In the synthesis of thioretinamide and thioretinaco, therefore, both the D and L isomers are expected to possess biological activity when incorporated into thioretinaco ozonide. It is also well known that certain isomers and derivatives of retinoic acid, especially 13 cis-retinoic acid, etretinate, and alpha retinoic acid, have biological activity. These retinoid isomers and derivatives are also expected to have biological activity when incorporated in place of retinoic acid into thioretinaco ozonide.

A large number of different corrinoid derivatives of cobalamin, in which various parts of the molecule have been modified, have been reported in the literature. Some of the more important examples of these analogues and derivatives are cobrynamide, cobinamide, cobamide, substituted amides of cobalamin, and derivatives resulting from substitution of the base of the nucleotide moiety of cobalamin, such as pseudovitamin B12 (adenine substitution), factor A (2-methyladenine substitution), factor III (5-hydroxybenzimidazole substitution) and factor C (guanine substitution). Many of these corrinoid derivatives have varying degrees of biological activity. These corrinoid derivatives are expected to have biological activity when incorporated in place of cobalamin into thioretinaco ozonide.

Certain derivatives of cholestanol, such as cholestanol acetate, cholestanol benzoate, and cholestanol hemisuccinate, are expected to function satisfactorily as constituents of ozone-resistant liposomes in the invention. The other major saturated sterol isomer, coprostanol and its derivatives, coprostanol acetate, coprostanol benzoate, and coprostanol hemisuccinate, are also expected to function satisfactorily as constituents of ozone-resistant liposomes.

Many pharmaceutical, neutraceutical, and other compounds and enzymes with oxidation-reduction properties are expected to cause oxidative damage to liposomes containing unsaturated lipid constituents. Accordingly, the use of ozone-resistant liposomes, as described in the invention, is expected to enhance the biological and pharmacological activities of these compounds. Examples of this class of compounds include semidehydroascorbate, dehydroascorbate, ascorbate, nitric oxide, ozone, peroxynitrite, peroxynitrate, superoxide, hydrogen peroxide, hydroxyl radical, singlet oxygen, radical complexes of transition metals such as cuprein, ceruloplasmin, ferritin, and cobalamin, lipid epoxides, lipid hydroperoxides, lipid alkoxyl radicals, lipid peroxyl radicals, enals (alpha-beta unsaturated aldehydes), N-tert-butyl alpha phenyl nitrone (PBN, a radical trapping compound that prolongs lifespan of animals), and oxidation-reduction enzymes, such as NAD(P)H oxidases, superoxide dismutases, glutathione peroxidase, NAD quinone reductase, dehydrogenases, cytochrome P450 reductase, mixed function oxidases, and catalase.

The novel compounds as heretofore described and the processes for their use by delivery of specialized ozone-resistant or ozone-resistant sterically stabilized liposomes that demonstrate anticarcinogenic, antineoplastic, antiatherogenic, antiviral, and anti aging activities are expected to be effective in preventing chemically induced tumors in laboratory mice, diminishing growth of malignant tumors in laboratory mice, preventing arteriosclerosis in laboratory rabbits, diminishing the replication of a virus in cultured mouse cells, and increasing the life span of laboratory rats. The compounds and processes of the invention are also considered to have value as therapeutic agents and treatments in preventing human cancer, decreasing the growth of human malignant tumors, preventing human arteriosclerotic plaques, diminishing the replication of human pathogenic viruses, preventing the degenerative tissue abnormalities associated with human aging, and extending the human life span.

The invention as heretofore described is useful in treatment and prevention of neoplastic, atherosclerotic, and viral diseases in mammals generally, and specifically in human subjects. The range of effective concentration of thioretinaco ozonide oxygen ATP disulfonium complex within ozone-resistant liposomes and within ozone-resistant sterically stabilized liposomes is broad, extending from 0.1–60 mg/kg of body weight. The novel therapeutic compounds of the invention can be administered to mammals or human subjects in the aforesaid dosage range. Such administration can be in a variety of compatible, non-toxic solvents and vehicles that do not cause dissociation or inactivation of the thioretinaco ozonide oxygen ATP disulfonium complex within specialized liposomal carriers. The novel therapeutic compounds of the invention can be administered by the enteric route, employing capsules, tablets, and time-release formulations, mixed with suitable inert carriers. The novel therapeutic compounds of the invention can also be administered parenterally in compatible solvents and vehicles, given intravenously, intramuscularly, intraperitoneally, subcutaneously, intracisternally, intrathecally, and within neoplasms in various internal organs by direct injection, with ultrasound, nuclear magnetic resonance imaging, or X-ray computerized tomography guidance. The novel therapeutic compounds of the invention can also be applied topically in suitable solvents and carriers directly to cutaneous neoplasms or proliferative papulosquamous, viral, or inflammatory skin lesions.

As will be recognized by those skilled in the art, the invention is susceptible to a broad range of modifications without departing from its spirit or essential characteristics. The described embodiments are to be considered in all respects as illustrative and not restrictive. Those skilled in the art will recognize that specific applications can result in variation, the novel carrier and medicaments of the invention without departing from the spirit and scope of the invention as embodied in the following claims.

I claim:

1. A liposomal preparation comprising:
   (a) an ozone resistant liposome;
   (b) a medicament having the formula:
      N-homocysteine thiolactonyl retinamido cobalamin ozonide oxygen adenosine triphosphate disulfonium complex $(NHTR)_2$ Cbl $O_3$ $O_2$ ATP,
   wherein:
      NHTR is N-homocysteine thiolactonyl retinamide;
      Cbl is cobalamin;
      $O_3$ is zone;
      $O_2$ is oxygen; and
      ATP is adenosine triphosphate.

2. The liposomal preparation of claim 1 wherein said ozone resistant liposome is composed of at least one member selected from the group consisting of glycolipids, phosphatides and sterols.

3. The liposomal preparation of claim 1 wherein all the carbon—carbon double bonds of said ozone resistant liposome are fully saturated with hydrogen.

4. The liposomal preparation of claim 1 wherein said ozone resistant liposome contains at least one member selected from the group consisting of:
   (1) hydrogenated phosphoinositol (HPI);
   (2) distearoyl phosphatidylcholine (DSPC);
   (3) cholestanol (CHA); and
   (4) coenzyme Q10 (Q10).

5. The liposomal preparation of claim 4 wherein said ozone resistant liposome is formed from hydrogenated phosphoinositol (HPI), distearoyl phosphatidylcholine (DSPC), cholestanol (CHA) and coenzyme Q10 (Q10).

6. The liposomal preparation of claim 1 wherein said ozone resistant liposome is a sterically stabilized liposome.

* * * * *